US009153934B2

(12) United States Patent
Takada et al.

(10) Patent No.: US 9,153,934 B2
(45) Date of Patent: Oct. 6, 2015

(54) LASER APPARATUS, LIGHT THERAPY APPARATUS, EXPOSURE APPARATUS, DEVICE MANUFACTURING METHOD, AND OBJECT INSPECTION APPARATUS

(75) Inventors: Yasutoshi Takada, Kawasaki (JP); Akira Tokuhisa, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 1081 days.

(21) Appl. No.: 13/075,486

(22) Filed: Mar. 30, 2011

(65) Prior Publication Data

US 2011/0245898 A1  Oct. 6, 2011

Related U.S. Application Data

(63) Continuation of application No. PCT/JP2009/005200, filed on Oct. 7, 2009.

(30) Foreign Application Priority Data

Oct. 10, 2008  (JP) .................................. 2008-264499

(51) Int. Cl.
*H01S 3/00*  (2006.01)
*A61N 5/067*  (2006.01)
(Continued)

(52) U.S. Cl.
CPC .............. *H01S 3/2383* (2013.01); *A61F 9/008* (2013.01); *A61F 9/00804* (2013.01); *G02F 1/3532* (2013.01); *H01S 3/06754* (2013.01); *A61F 2009/00872* (2013.01); *H01S 3/0092* (2013.01)

(58) Field of Classification Search
CPC ............. G02F 1/00; G02F 1/35; G02F 1/353; G02F 1/3532; H01S 3/0085; H01S 3/23; H01S 3/2308; A61N 5/06; A61N 5/062; A61N 5/065; A61N 5/067; A61N 2005/0658
USPC .............. 372/9, 20, 25, 29.01, 34, 69, 70, 75; 359/237, 245, 248, 249, 288, 325, 326, 359/330; 607/88, 89
See application file for complete search history.

(56) References Cited

U.S. PATENT DOCUMENTS 5,606,453 A * 2/1997 Walling et al. ................ 359/330
6,021,141 A * 2/2000 Nam et al. ...................... 372/20
(Continued)

FOREIGN PATENT DOCUMENTS

JP       A-7-318997        12/1995
JP       A-2001-352116     12/2001
(Continued)

OTHER PUBLICATIONS

International Search Report dated Nov. 10, 2009 in corresponding International Application No. PCT/JP2009/005200 (with translation).

(Continued)

*Primary Examiner* — Ahmed Farah
(74) *Attorney, Agent, or Firm* — Oliff PLC

(57) ABSTRACT

A fundamental wavelength light generating unit generates light of a fundamental wavelength in accordance with an output wavelength instruction signal. An optical amplifier unit amplifies the light of the fundamental wavelength. A wavelength converting part includes nonlinear optical crystals that each perform wavelength conversion and temperature regulators that each regulate the temperature of the corresponding nonlinear optical crystal, wherein the wavelength converting part converts the light amplified by the optical amplifier unit to light of the wavelength indicated by the output wavelength instruction signal. A storage unit stores correspondence information that indicates a correspondence relationship between the wavelength of the output light and the temperature of each of the nonlinear optical crystals based on the corresponding wavelength. A control unit controls each of the temperature regulators such that the temperature of the corresponding nonlinear optical crystal reaches the temperature to be set in accordance with the output wavelength instruction signal.

13 Claims, 7 Drawing Sheets

(51) Int. Cl.
*H01S 3/23* (2006.01)
*A61F 9/008* (2006.01)
*G02F 1/35* (2006.01)
*H01S 3/067* (2006.01)

(56) References Cited

U.S. PATENT DOCUMENTS

| | | | | |
|---|---|---|---|---|
| 6,636,537 | B2 * | 10/2003 | Takada | 372/23 |
| 7,397,598 | B2 * | 7/2008 | Tokuhisa et al. | 359/326 |
| 7,573,921 | B2 * | 8/2009 | Yumoto et al. | 372/22 |

FOREIGN PATENT DOCUMENTS

| | | |
|---|---|---|
| JP | 2005-327823 A | 11/2005 |
| JP | A-2007-64809 | 3/2007 |
| JP | A-2007-233039 | 9/2007 |
| JP | A-2008-40293 | 2/2008 |
| WO | WO 01/20397 A1 | 3/2001 |

OTHER PUBLICATIONS

Office Action dated Jul. 10, 2014 issued in Taiwanese Patent Application No. 098134227 (with translation).
Nov. 30, 2012 Office Action issued in Japanese Application No. 2008-264499.
Apr. 24, 2013 Final Decision issued in Japanese Application No. 2008-264499.
Temperature-Tined 90° Phase-Matching Propoerties of LiB3O5. IEEE Journal of Quantum Electronic vol. 30 No. 12 December, pp. 2950-2952.
Quasi-Phase-Matched Optical Parametric Oscillation with Periodically Poled Stoichiometric LiTaO3, May 1, 2000, vol. 25, No. 9, Optics Letters, pp. 651-653.
Type-I and Type-II Noncritical Phase Matching of LiB3O5 Crystal, J Appl. Phys. 73 (11), Jun. 1, 1993, pp. 7108-7110.
Nov. 10, 2009 Written Opinion issued in Japanese Application No. PCT/JP2009/005200.

\* cited by examiner

LASER APPARATUS, LIGHT THERAPY APPARATUS, EXPOSURE APPARATUS, DEVICE MANUFACTURING METHOD, AND OBJECT INSPECTION APPARATUS

RELATED ART

The present invention relates to a laser apparatus and to a light therapy apparatus, an exposure apparatus, a device manufacturing method, and an object inspection apparatus that uses such a laser apparatus.

RELATED ART

Patent Document 1 below discloses a laser apparatus that comprises: a laser light generating unit, which generates laser light of a single wavelength that falls within the wavelength range of the infrared region to the visible region; an optical amplifier unit, which comprises an optical fiber amplifier that amplifies the laser light generated by the laser light generating unit; a plurality of nonlinear optical crystals, wherein each of the nonlinear optical crystals performs wavelength conversion of the laser light amplified by the optical amplifier unit; and a wavelength converting part, which comprises a plurality of temperature control apparatuses, wherein the temperature control apparatuses control the temperatures of the nonlinear optical crystals in order to adjust their phase matching angles during wavelength conversion; furthermore, the laser apparatus generates ultraviolet light from the wavelength converting part. Controlling the temperatures via the temperature control apparatuses adjusts the phase matching angles of all of the nonlinear crystals, which makes it possible to increase conversion efficiency using simple control.

In addition, page 19 through page 21 in Patent Document 1 recites that a DFB semiconductor laser is used as the laser light generating unit, and that either the oscillation wavelength may be stabilized and kept at a constant wavelength by controlling the temperature of the DFB semiconductor laser or the output wavelength can be adjusted by actively varying that oscillation wavelength.

PRIOR ART LITERATURE

Patent Documents

Patent Document 1: Reissued Patent No. WO2001/020397

OVERVIEW OF THE INVENTION

Problems Solved by the Invention

Nevertheless, in a laser apparatus of the type discussed above, even if a DFB semiconductor laser is used as the laser light generating unit and the output wavelength can be adjusted by actively varying the oscillation wavelength, which is achieved by controlling the temperature of the DFB semiconductor laser, the tuning range of the output wavelength of the laser apparatus is relatively narrow and achieving adequate wavelength tuning performance is difficult, both of which are problems.

The present invention considers such circumstances, and it is an object of the present invention to provide a laser apparatus that can expand the tunable wavelength range of output light, and to provide a light therapy apparatus, an exposure apparatus, a device manufacturing method, and an object inspection apparatus that uses such a laser apparatus.

Means for Solving the Problems

Means for solving the aforementioned problems are presented in the aspects below. A laser apparatus according to a first aspect of the invention is a laser apparatus that outputs tunable wavelength output light and that comprises: (i) a fundamental wavelength light generating unit, which generates light of a fundamental wavelength in accordance with an output wavelength instruction signal that specifies the wavelength of the output light; (ii) an optical amplifier unit, which amplifies the light of the fundamental wavelength; (iii) a wavelength converting part that comprises a plurality of nonlinear optical crystals, each nonlinear optical crystal performing wavelength conversion, and a plurality of temperature regulators, each temperature regulator regulating the temperature of the corresponding nonlinear optical crystal, wherein the wavelength converting part converts the light amplified by the optical amplifier unit to light of the wavelength indicated by the output wavelength instruction signal; (iv) a storage unit, which stores correspondence information that indicates a correspondence relationship between the wavelength of the output light and the temperature of each of the nonlinear optical crystals to be set in accordance with the corresponding wavelength; and (v) a control unit that controls each of the temperature regulators such that the temperature of the corresponding nonlinear optical crystal reaches the temperature to be set as determined by the correspondence information in accordance with the output wavelength instruction signal.

A light therapy apparatus according to a second aspect of the invention comprises: a laser apparatus according to the first aspect of the invention; and a radiation optical system, which guides and radiates output light output from the laser apparatus to a therapy region.

An exposure apparatus according to a third aspect of the invention is an exposure apparatus, which transfers a pattern of a mask to a photosensitive object, that comprises: a laser apparatus according to the first aspect of the invention; an illumination optical system, which radiates output light output from the laser apparatus to the mask; and a projection optical system, which projects light from the mask to the photosensitive object.

A device fabricating method according to a fourth aspect of the invention is a device fabricating method, which includes a lithographic process, that comprises the step of: using the exposure apparatus according to the third aspect of the invention to transfer, in the lithographic process, the pattern of the mask to the photosensitive object.

An object inspection apparatus according to a fifth aspect of the invention comprises: a laser apparatus according to the first aspect of the invention; a support part, which supports an object to be inspected; a detector, which detects a projected image of the object to be inspected; an illumination optical system, which radiates output light output from the laser apparatus to the object to be inspected; and a projection optical system, which projects light from the object to be inspected to the detector.

Effects of the Invention

The present invention provides a laser apparatus that can expand the tunable wavelength range of output light, and provides a light therapy apparatus, an exposure apparatus, a device manufacturing method, and an object inspection apparatus that uses such a laser apparatus.

DETAILED DESCRIPTION OF THE PREFERRED EMBODIMENTS

A laser apparatus, a light therapy apparatus, an exposure apparatus, a device manufacturing method, and an object inspection apparatus according to the present invention will now be explained, referencing the drawings.

[First Embodiment]

Figure 1:
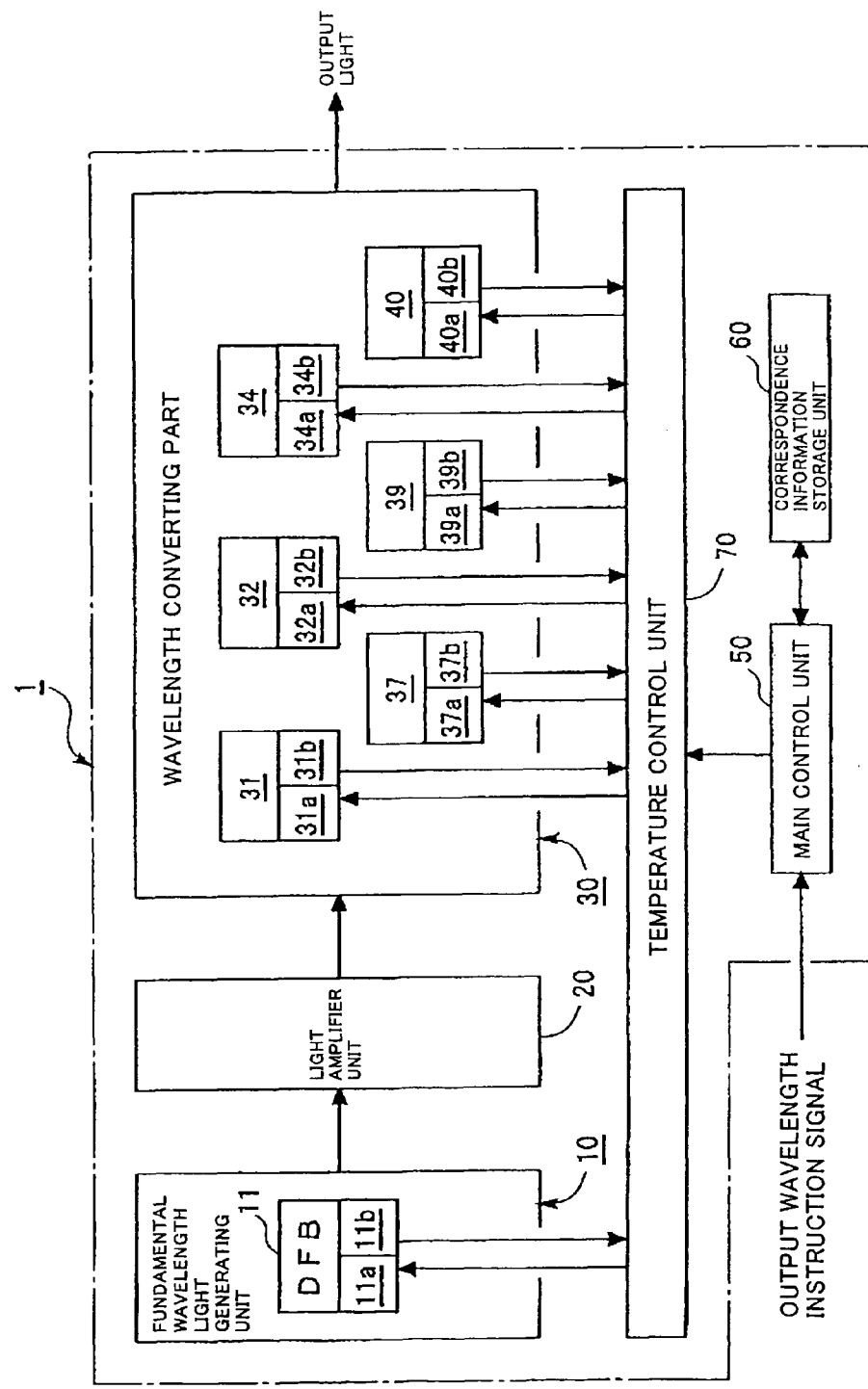
FIG. 1 is a schematic block diagram that shows a laser apparatus according to a first embodiment of the present invention.
Figure 2:
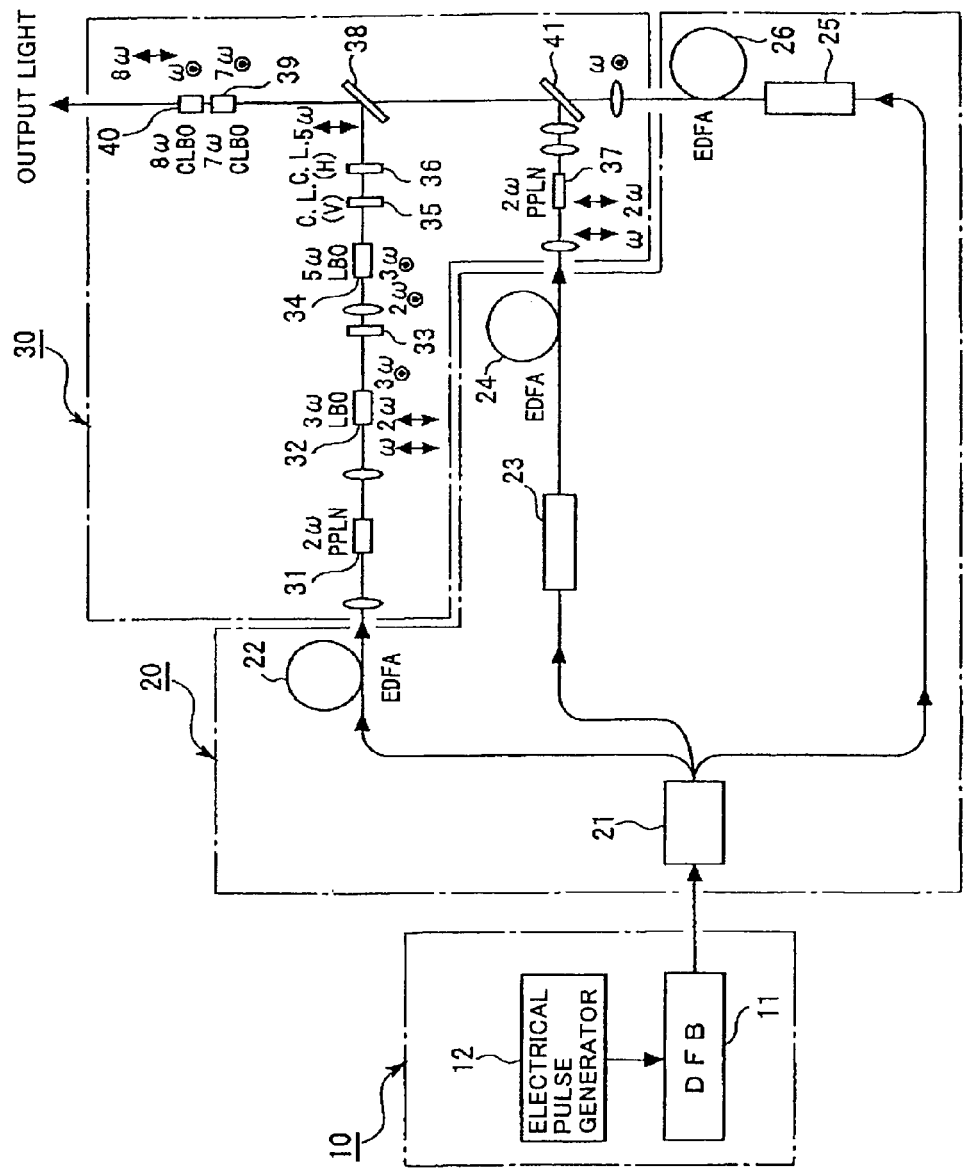
FIG. 2 is a diagram that shows a fundamental wavelength light generating unit, an optical amplifier unit, and a wavelength converting part, each of which is shown in FIG. 1.

FIG. 1 is a schematic block diagram that shows a laser apparatus 1 according to a first embodiment of the present invention. FIG. 2 is a diagram that shows a fundamental wavelength light generating unit 10, an optical amplifier unit 20, and a wavelength converting part 30, each of which is shown in FIG. 1. FIG. 1 shows only those constituent elements of the fundamental wavelength light generating unit 10 and the wavelength converting part 30 that are related to temperature control. Moreover, in FIG. 2, among the constituent elements of the fundamental wavelength light generating unit 10 and the wavelength converting part 30, temperature regulators 31a, 32a, 34a, 37a, 39a, 40a and temperature detectors 31b, 32b, 34b, 37b, 39b, 40b are omitted.

The laser apparatus 1 according to the present embodiment outputs output light of a tunable wavelength and, as shown in FIG. 1, comprises: the fundamental wavelength light generating unit 10; the optical amplifier unit 20; the wavelength converting part 30; a main control unit 50; a correspondence information storage unit 60, which comprises nonvolatile memory and the like; and a temperature control unit 70.

The fundamental wavelength light generating unit 10 is configured such that light of the fundamental wavelength is generated in accordance with an output wavelength instruction signal, which specifies the wavelength of the output light of the laser apparatus 1. In the present embodiment, the main control unit 50 receives the output wavelength instruction signal from a source external to the laser apparatus 1, but the present invention is not limited thereto. For example, if a user, an installer, or the like specifies the wavelength of the output light of the laser apparatus 1, then the output wavelength instruction signal may be issued by, for example, a potentiometer that is installed in the laser apparatus 1.

In the present embodiment, as shown in FIG. 1 and FIG. 2, the fundamental wavelength light generating unit 10 is configured as a temperature controlled tunable laser light source and comprises: a DFB (distributed feedback) semiconductor laser 11; a laser light source temperature regulator 11a, such as a Peltier device, that regulates the temperature of the DFB semiconductor laser 11; a temperature detector 11b, such as a thermistor, that detects the temperature of the DFB semiconductor laser 11; and an electrical pulse generator 12.

An InGaAsP DFB semiconductor laser, for example, that can tune its oscillation wavelength within a prescribed range that includes 1.547 μm is used as the DFB semiconductor laser 11. The electrical pulse generator 12 is a driver that controls the operation of the DFB semiconductor laser 11 and, for example, pulses a drive signal with a pulse width of approximately 1 ns and a repetition frequency f equal to several tens to several hundreds of kilohertz and supplies such to the DFB semiconductor laser 11. Thereby, the DFB semiconductor laser 11 outputs to the optical amplifier unit 20 pulsed light of the fundamental wavelength (i.e., light of the fundamental wave) with a peak power of approximately 10 mW.

Correspondence information that indicates the correspondence relationship between the wavelength of the output light of the laser apparatus 1 and the temperature of the DFB semiconductor laser 11 needed to output the output light at that wavelength from the laser apparatus 1 (hereinbelow, called the "output wavelength and laser temperature correspondence relationship") is stored in advance in the correspondence information storage unit 60. In the present embodiment, as discussed below, the wavelength converting part 30 outputs light of a wavelength that is ⅛ the wavelength of the fundamental wave output by the fundamental wavelength light generating unit 10 as the output light of the laser apparatus 1. Accordingly, the wavelength of the fundamental wave output by the fundamental wavelength light generating unit 10 must be eight times the wavelength of the output light of the laser apparatus 1. As is well known in the art, the wavelength of the output light of the DFB semiconductor laser 11 can be adjusted by varying the temperature of the DFB semiconductor laser 11. Accordingly, in the present embodiment, the correspondence information that indicates the correspondence relationship between the wavelength of the output light of the laser apparatus 1 and the temperature of the DFB semiconductor laser 11 when the DFB semiconductor laser 11 generates light with a wavelength that is eight times the wavelength of the output light of the laser apparatus 1 is stored in the correspondence information storage unit 60 as the output wavelength and laser temperature correspondence relationship. There are individual differences in the correspondence relationship between the temperature of the DFB semiconductor laser 11 and the wavelength of the output light of the DFB semiconductor laser 11. Consequently, it is preferable to obtain the output wavelength and laser temperature correspondence relationship, in advance, based on the temperature detected by the temperature detector 11b while the temperature regulation state of the temperature regulator 11a is successively changed and on the result of actually measuring the wavelength of the output light of the DFB semiconductor laser 11. The correspondence information that indicates the output wavelength and laser temperature correspondence relationship may be stored in the correspondence information storage unit 60 in the form of an approximation expression or a lookup table.

When controlling the temperature of the DFB semiconductor laser 11, the main control unit 50 references the correspondence information stored in the correspondence information storage unit 60 based on the output wavelength instruction signal in order to acquire the temperature of the DFB semiconductor laser 11 to be set in accordance with the output wavelength indicated by the output wavelength instruction signal, and supplies that temperature to the temperature control unit 70 as the target temperature of the DFB semiconductor laser 11. The temperature control unit 70 performs feedback control such that the temperature of the DFB semiconductor laser 11 reaches the target temperature by supplying an adjustment signal to the temperature regulator 11a in accordance with the target temperature and a detection signal output from the temperature detector 11b.

Based on this temperature control, the DFB semiconductor laser 11 (and, in turn, the fundamental wavelength light generating unit 10) generates light of the fundamental wavelength in accordance with the output wavelength instruction signal. Thus, in the present embodiment, the fundamental wavelength light generating unit 10 is configured as a temperature controlled wavelength tunable laser light source, but it may be configured as a wavelength tunable laser light source of some other type. For example, the oscillation wavelength of the laser light source may be varied by disposing inside a resonator of the laser light source an optical system for setting the oscillation wavelength and varying the optical path length of a prescribed portion inside that optical system.

As shown in FIG. 2, the optical amplifier unit 20 comprises: a coupler 21, which splits the light of the fundamental wave generated by the fundamental wavelength light generating unit 10 into three parts; a first EDFA 22, which serves as an optical amplifier that amplifies one of the lights resulting from the split; a retarder 23, which retards another one of the lights resulting from the split; a second EDFA 24, which serves as an optical amplifier that amplifies the light retarded by the retarder 23; a retarder 25, which retards the one remaining light resulting from the split; and a third EDFA 26, which serves as an optical amplifier that amplifies the light retarded by the retarder 25.

Next, the wavelength converting part 30 will be explained. As shown in FIG. 1 and FIG. 2, the wavelength converting part 30 comprises: a plurality of nonlinear optical crystals 31, 32, 34, 37, 39, 40, wherein each of the nonlinear optical crystals performs wavelength conversion; and the plurality of temperature regulators 31a, 32a, 34a, 37a, 39a, 40a, wherein each of the temperature regulators is, for example, a heater that regulates the temperature of the corresponding nonlinear optical crystal; furthermore, the light amplified by the optical amplifier unit 20 is converted to light of the wavelength indicated by the output wavelength instruction signal. The temperature detectors 31b, 32b, 34b, 37b, 39b, 40b, which are thermistors, are provided to and detect the temperatures of the nonlinear optical crystals 31, 32, 34, 37, 39, 40, respectively.

In the present embodiment, a PPLN crystal that constitutes a second harmonic wave generating optical element is used as the nonlinear optical crystal 31. A PPKTP crystal, a PPSLT crystal, an LBO crystal, or the like may be used as the nonlinear optical crystal 31. An LBO crystal that constitutes a third harmonic wave generating optical element is used as the nonlinear optical crystal 32. An LBO crystal that constitutes a fifth harmonic wave generating optical element is used as the nonlinear optical crystal 34. A BBO crystal or a CBO crystal may be used as the nonlinear optical crystal 34. A PPLN crystal that constitutes a second harmonic wave generating optical element is used as the nonlinear optical crystal 37. A PPKTP crystal, a PPSLT crystal, an LBO crystal, or the like may be used as the nonlinear optical crystal 37. A CLBO crystal that constitutes a seventh harmonic wave generating optical element is used as the nonlinear optical crystal 39. A CLBO crystal that constitutes an eighth harmonic wave generating optical element is used as the nonlinear optical crystal 40.

In FIG. 2, elements indicated by elliptical shapes are collimator lenses, condenser lenses, and the like, and explanations thereof are omitted. In addition, in FIG. 2, P polarized lights are indicated by arrows, and S polarized lights are indicated by a dot in a circle; furthermore, the fundamental wave is denoted as $\omega$ and the $n^{th}$ harmonic wave is denoted as $n\omega$.

As shown in FIG. 2, the fundamental wave of the P polarized light amplified by the first EDFA 22 enters the nonlinear optical crystal 31 (i.e., a second harmonic wave generating optical element), and what emerges from the nonlinear optical crystal 31 is the second harmonic wave of the P polarized light, along with the fundamental wave. The fundamental wave and the second harmonic wave enter the nonlinear optical crystal 32 (i.e., a third harmonic wave generating optical element). What emerges from the nonlinear optical crystal 32 is the third harmonic wave of the S polarized light, along with the fundamental wave and the second harmonic wave.

These lights pass through a double wavelength waveplate 33, and thereby only the second harmonic wave is converted to S polarized light. As the double wavelength waveplate 33, for example, a waveplate is used that consists of a uniaxial crystalline flat plate that is cut parallel to the optical axis of the crystal. The waveplate (i.e., the crystal) is cut such that its thickness is an integer multiple of $\lambda/2$ with respect to the light of one wavelength (i.e., the second harmonic wave) and is an integer multiple of $\lambda$ with respect to the light of another wavelength such that the polarization of the light of the one wavelength is rotated and the polarization of the light of the other wavelength is not rotated. Furthermore, the second harmonic wave and the third harmonic wave, both of which have become S polarized lights, enter the nonlinear optical crystal 34 (i.e., a fifth harmonic wave generating optical element). What emerges from the nonlinear optical crystal 34 is the fifth harmonic wave of the P polarized light, along with the second harmonic wave and the third harmonic wave. Furthermore, the fundamental wave of the P polarized light transmits through the nonlinear optical crystal 34 as is.

Because of the effects of walk-off, the cross section of the fifth harmonic wave generated by the nonlinear optical crystal 34 has an elliptical shape that, if left as is, will degrade convergence and cannot be used in the next wavelength conversion. Accordingly, cylindrical lenses 35, 36 shape the cross section from the elliptical shape into a circular shape.

Moreover, the fundamental wave of the P polarized light amplified by the second EDFA 24 enters the nonlinear optical crystal 37 (i.e., a second harmonic wave generating optical element), and what emerges from the nonlinear optical crystal 37 is the second harmonic wave of the P polarized light, along with the fundamental wave.

Furthermore, the fundamental wave of the S polarized light amplified by the third EDFA 26 is combined by a dichroic mirror 41 with the second harmonic wave of the P polarized light discussed above. In this example, the dichroic mirror 41 transmits the fundamental wave and reflects the second harmonic wave. The combined fundamental wave of the S polarized light and second harmonic wave of the P polarized light is further combined with the fifth harmonic wave of the P polarized light discussed above by a dichroic mirror 38. In this example, the dichroic mirror 38 transmits the fundamental wave and the second harmonic wave and reflects the fifth harmonic wave. A bulk optical element can be used for combining these lights; for example, a color separating and combining mirror (i.e., a dichroic mirror), a reflective diffractive optical element, a transmissive diffractive optical element, and the like can be used.

The combined fundamental wave of the S polarized light, the second harmonic wave of the P polarized light, and the fifth harmonic wave of the P polarized light enters the nonlinear optical crystal 39 (i.e., a seventh harmonic wave generating optical element), and what emerges from the nonlinear optical crystal 39 is the seventh harmonic wave of the S polarized light, along with these lights. These lights enter the nonlinear optical crystal 40 (i.e., an eighth harmonic wave generating optical element); here, the fundamental wave of the S polarized light and the seventh harmonic wave of the S polarized light combine, and the eighth harmonic wave of the P polarized light is generated. A dichroic mirror, a polarizing beam splitter, a prism, or the like can be used if one desires to isolate just the eighth harmonic wave from the lights of other wavelengths that emerge from the nonlinear optical crystal 40. In the present embodiment, a dichroic mirror, a polarizing beam splitter, a prism, or the like (not shown) is used to isolate the eighth harmonic wave (i.e., light with ⅛ the wavelength of the fundamental wavelength) from the lights that emerge from the nonlinear optical crystal 40, and such is output as the output light of the wavelength converting part 30. In the present embodiment, the output light of the wavelength converting part 30 serves as the output light of the laser apparatus 1. In the present embodiment, the output light of the laser apparatus 1 is thereby ultraviolet pulsed light that is tunable wavelength within a prescribed range that includes a wavelength equal to ⅛ of 1.547 μm (i.e., 193.4 nm).

The wavelength of the incident light that impinges each of the nonlinear optical crystals 31, 32, 34, 37, 39, 40 is determined only by the fundamental wavelength generated by the fundamental wavelength light generating unit 10 and is not dependent on the temperatures of the nonlinear optical crystals 31, 32, 34, 37, 39, 40. Accordingly, the wavelength of the output light of the wavelength converting part 30 does not depend on the temperatures of the nonlinear optical crystals 31, 32, 34, 37, 39, 40; furthermore, even if those temperatures vary, the wavelength output by the wavelength converting part 30 does not change, namely, it remains ⅛ of the fundamental wavelength generated by the fundamental wavelength light generating unit 10. However, if the fundamental wavelength generated by the fundamental wavelength light generating unit 10 varies in accordance with the output wavelength instruction signal as discussed above, then the wavelength of the incident light that accordingly impinges the nonlinear optical crystals 31, 32, 34, 37, 39, 40 varies, as does the wavelength of the output light of the wavelength converting part 30, and thereby the wavelength tunability of the output light of the laser apparatus 1 is achieved.

Figure 3:
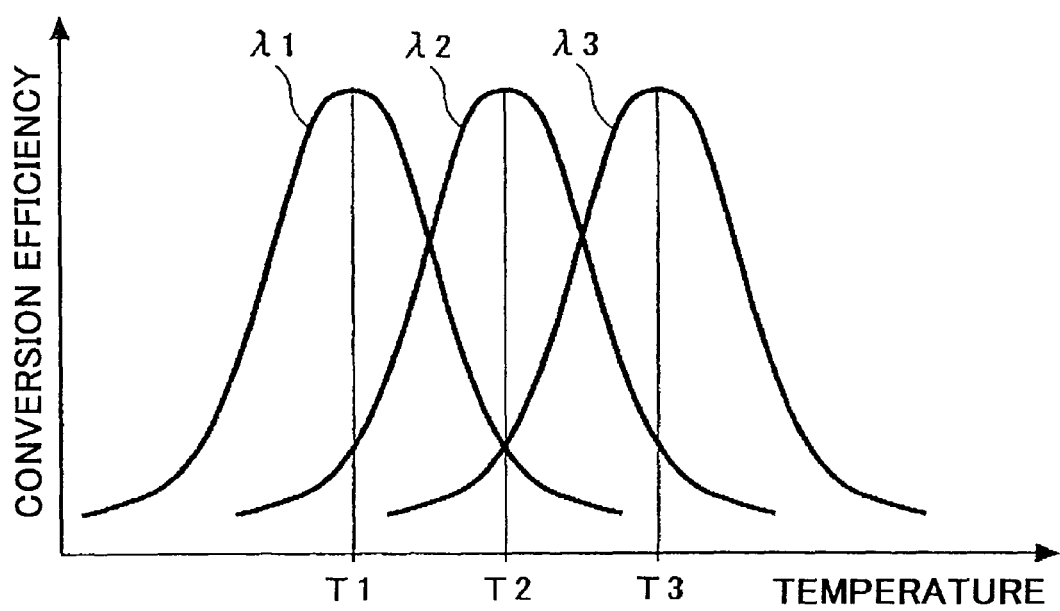
FIG. 3 is a diagram that shows the characteristics of a nonlinear optical crystal.

As shown in FIG. 3, the conversion efficiency of a nonlinear optical crystal depends not only on the temperature of the nonlinear optical crystal but also on the wavelength of the incident light that impinges the nonlinear optical crystal. FIG. 3 is a graph that schematically shows the temperature dependency of the conversion efficiency of the nonlinear optical crystal for wavelengths $\lambda 1$, $\lambda 2$, $\lambda 3$ of the incident light. In the example shown in FIG. 3, the conversion rate for the wavelength $\lambda 1$ is maximal at a temperature T1, the conversion rate for the wavelength $\lambda 2$ is maximal at a temperature T2, and the conversion rate for the wavelength $\lambda 3$ is maximal at a temperature T3.

Accordingly, even if the temperature of each of the nonlinear optical crystals 31, 32, 34, 37, 39, 40 is set such that the conversion efficiency of the relevant nonlinear optical crystal 31, 32, 34, 37, 39, 40 is maximal for a certain wavelength of the output light of the laser apparatus 1 (and, in turn, the fundamental wavelength generated by the fundamental wavelength light generating unit 10), if we assume that those temperatures are maintained continuously as is and that the wavelength of the output light of the laser apparatus 1 (and, in turn, the fundamental wavelength generated by the fundamental wavelength light generating unit 10) varies, then the wavelength of the light that impinges each of the nonlinear optical crystals 31, 32, 34, 37, 39, 40 will vary and, accordingly, the conversion efficiency of the nonlinear optical crystals 31, 32, 34, 37, 39, 40 will decrease. Furthermore, the larger the shift in that wavelength, the more the conversion efficiency of the nonlinear optical crystals 31, 32, 34, 37, 39, 40 will decrease, which is a problem. For example, if the temperature of the nonlinear optical crystal that has the characteristics shown in FIG. 3 is set to T2 such that the conversion efficiency is maximal when the incident light has the wavelength $\lambda 2$ and that temperature T2 is maintained continuously, then the wavelength of the incident light will shift from $\lambda 2$ toward the $\lambda 1$ side or toward the $\lambda 3$ side, thereby reducing the conversion efficiency of the nonlinear optical crystal; furthermore, the larger the shift in the wavelength, the greater the decrease in the conversion efficiency.

If the conversion efficiency of the nonlinear optical crystals 31, 32, 34, 37, 39, 40 decreases significantly, then the power level of the output light of the laser apparatus 1 will decrease significantly, making it unfit for use. Accordingly, even if the temperature of each of the nonlinear optical crystals 31, 32, 34, 37, 39, 40 is optimized for a given wavelength of the output light of the laser apparatus 1, the tuning range of the wavelength of the output light of the laser apparatus 1 will narrow if those temperatures are maintained continuously, which is a problem.

In contrast, in the present embodiment, even if the wavelength of the output light of the laser apparatus 1 (and, in turn, the fundamental wavelength generated by the fundamental wavelength light generating unit 10) is varied by the main control unit 50, the correspondence information storage unit 60, and the temperature control unit 70, that wavelength is tracked and the temperatures of the nonlinear optical crystals 31, 32, 34, 37, 39, 40 are each controlled such that those temperatures are optimized with respect to conversion efficiency. Accordingly, the tuning range of the wavelength of the output light of the laser apparatus 1 according to the present embodiment can be expanded significantly. This point is discussed in detail below.

In addition to the correspondence information that indicates the output wavelength and laser temperature correspondence relationship discussed above, the correspondence information that indicates the correspondence relationship between the wavelength of the output light of the laser apparatus 1 with respect to each of the nonlinear optical crystals 31, 32, 34, 37, 39, 40, on the one hand, and for each of the nonlinear optical crystals 31, 32, 34, 37, 39, 40 the temperature at which the conversion efficiency is maximal or near maximal for the wavelength of the light that impinges the given nonlinear optical crystal when the output light of that wavelength is output from the laser apparatus 1, on the other hand, (hereinbelow, called the "output wavelength and crystal temperature correspondence relationship") is also prestored in the correspondence information storage unit 60. For example, for a nonlinear optical crystal that has the characteristics shown in FIG. 3, if incident lights at the wavelengths $\lambda 1$, $\lambda 2$, $\lambda 3$, which correspond to first through third wavelengths of the output light of the laser apparatus 1, impinge the relevant nonlinear optical crystal, then correspondence information that indicates that the first through third wavelengths correspond to the temperatures T1, T2, T3, respectively, is stored in the correspondence information storage unit 60 as the correspondence information that indicates the output wavelength and crystal temperature correspondence relationship of the relevant nonlinear optical crystal. There are individual differences in the correspondence relationship between the wavelength of the incident light of the nonlinear optical crystal and the temperature at which the conversion efficiency is maximal. Consequently, it is preferable to obtain the output wavelength and crystal temperature correspondence relationship, in advance, based on the result of actually measuring the temperature detected by the temperature detector 11*b* and actually measuring the conversion efficiency while successively varying the temperature regulation state of the temperature regulator 11*a* as the wavelength of the incident light on each of the nonlinear optical crystals 31, 32, 34, 37, 39, 40 is successively varied. The correspondence information that indicates the output wavelength and crystal temperature correspondence relationship may be stored in the correspondence information storage unit 60 in the form of, for example, an approximation expression or a lookup table.

When controlling the temperatures of the nonlinear optical crystals 31, 32, 34, 37, 39, 40, the main control unit 50 references the correspondence information stored in the correspondence information storage unit 60 based on the output wavelength instruction signal in order to acquire the temperatures of the nonlinear optical crystals 31, 32, 34, 37, 39, 40 to be set in accordance with the output wavelength indicated by the output wavelength instruction signal, and supplies those temperatures to the temperature control unit 70 as the target temperatures of the nonlinear optical crystals 31, 32, 34, 37, 39, 40. The temperature control unit 70 performs feedback control such that the temperature of each of the nonlinear optical crystals 31, 32, 34, 37, 39, 40 reaches its target temperature by supplying, for each of the nonlinear optical crystals 31, 32, 34, 37, 39, 40, an adjustment signal to the temperature regulators 31*a*, 32*a*, 34*a*, 37*a*, 39*a*, 40*a* in accordance with the corresponding target temperature as well as in accordance with the detection signal output from the corresponding temperature detector 31*b*, 32*b*, 34*b*, 37*b*, 39*b*, 40*b*.

Accordingly, even if the wavelength of the output light of the laser apparatus 1 (and, in turn, the fundamental wavelength of the light output by the fundamental wavelength light generating unit 10) according to the present embodiment varies, that wavelength is tracked and the temperatures of the nonlinear optical crystals 31, 32, 34, 37, 39, 40 are each optimized with respect to conversion efficiency. Consequently, the tuning range of the wavelength of the output light of the laser apparatus 1 according to the present embodiment can be expanded. Thereby, according to the present embodiment, a sufficient wavelength tuning performance can be achieved.

[Second Embodiment]

Figure 4:
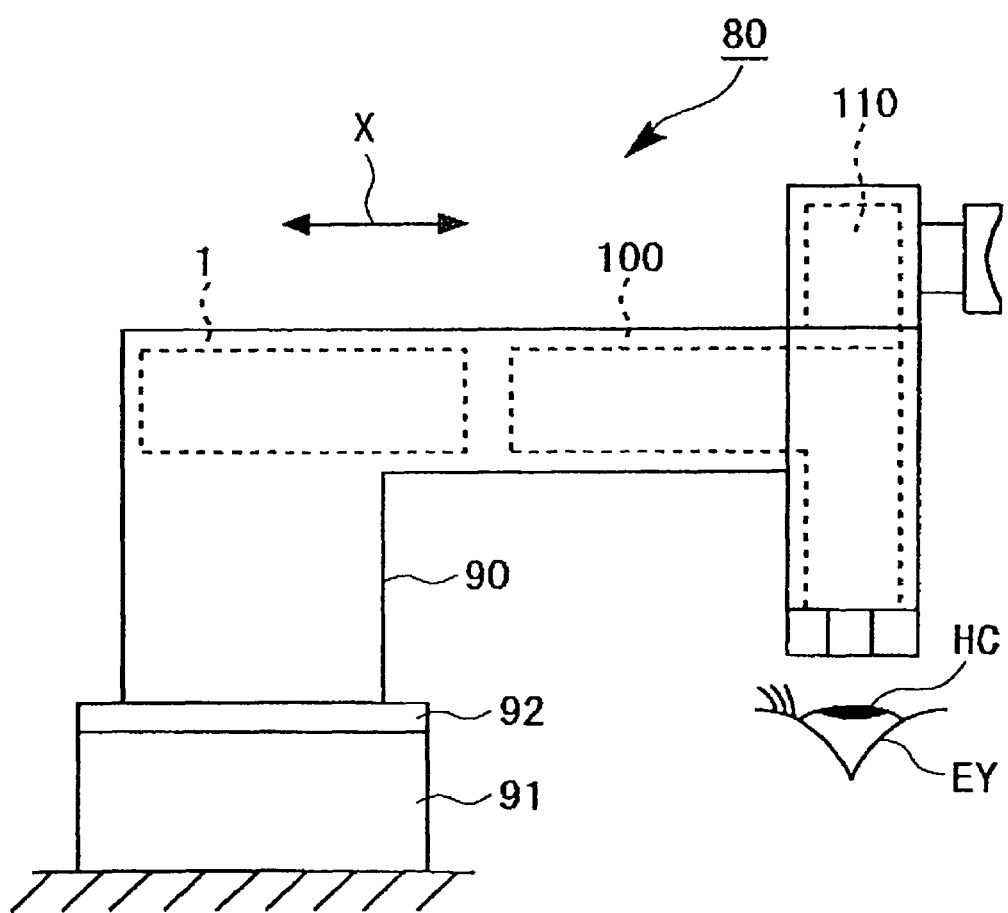
FIG. 4 is a schematic block diagram that shows a light therapy apparatus according to a second embodiment of the present invention.
Figure 5:
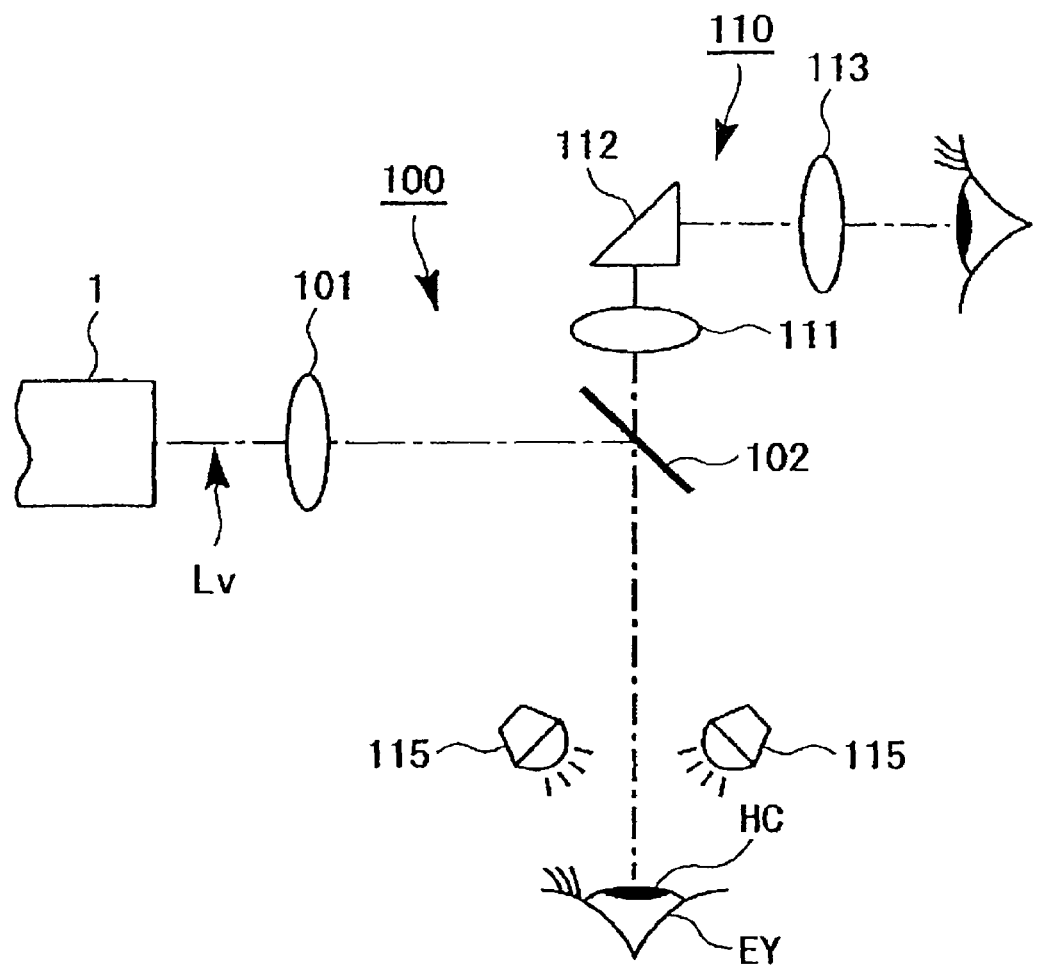
FIG. 5 is a schematic block diagram that shows a radiation optical system and an observation optical system that constitute the light therapy apparatus shown in FIG. 4.

FIG. 4 is a schematic block diagram that shows a light therapy apparatus 80 according to a second embodiment of the present invention. FIG. 5 is a schematic block diagram that shows a radiation optical system 100 and an observation optical system 110, which constitute the light therapy apparatus 80 shown in FIG. 4. The light therapy apparatus 80 according to the present embodiment is an apparatus that comprises and uses the laser apparatus 1 according to the first embodiment to correct cornea curvature or irregularity in order to treat myopia, astigmatism, and the like by radiating ultraviolet laser light (i.e., the output light of the laser apparatus 1) to a cornea and ablating either the corneal surface (i.e., in PRK; photorefractive keratectomy) or the interior of an incised cornea (i.e., in LASIK; laser intrastromal keratomileusis).

As shown in FIG. 4, the light therapy apparatus 80 basically comprises, inside an apparatus casing 90, the laser apparatus 1 discussed above; the radiation optical system 100, which guides and radiates ultraviolet laser light Lv output from the laser apparatus 1 to a surface (i.e., a therapy region) of a cornea HC of an eyeball EY; and the observation optical system 110, which observes the therapy region.

The apparatus casing 90 is provided and disposed on a base part 91 with an XY motion table 92 interposed therebetween; furthermore, the entire apparatus casing 90 is configured moveably with respect to the eyeball EY in the arrow X directions in FIG. 4, namely, in the lateral directions in the drawing, as well as in the Y directions perpendicular to the paper surface.

FIG. 5 shows the configuration of the radiation optical system 100 and the observation optical system 110. The radiation optical system 100 comprises: a condenser lens 101, which condenses the ultraviolet laser light Lv emitted from the laser apparatus 1 such that it forms a prescribed spot diameter on the eyeball EY; and a dichroic mirror 102, which reflects the ultraviolet laser light Lv from the condenser lens 101 and radiates such to the surface of the cornea HC of the eyeball EY, namely, the therapy target. The dichroic mirror 102 is set such that it reflects light in the ultraviolet region and transmits light in the visible region; furthermore, the dichroic mirror 102 can reflect the ultraviolet laser light Lv coaxially with the optical axis of the observation optical system 110 and can radiate such to the surface of the cornea HC as discussed later.

Moreover, the observation optical system 110 comprises: illumination lamps 115 that illuminate the surface of the cornea HC of the eyeball EY, which constitutes the therapy target; an objective 111, which receives light in the visible region that was radiated by the illumination lamps 115, reflected by the cornea HC, and transmitted through the dichroic mirror 102; a prism 112, which reflects the light from the objective 111; and an eyepiece 113, which receives the reflected light from the prism 112 and forms an image; furthermore, the observation optical system 110 is configured such that an enlarged image of the cornea HC from the light that passes through the eyepiece 113 can be observed.

Thereby, a specialist, such as an ophthalmologist, can perform light therapy while visually observing the therapy target via the observation optical system 110. For example, while the eyeball EY is being visually observed, the apparatus casing 90 is moved in the X directions and the Y directions, the ultraviolet laser light Lv is radiated as a spot light to the surface of the cornea HC, which is the therapy target, and thereby the radiated area is ablated. In addition, corrective therapy, such as the correction of myopia, astigmatism, and farsightedness, can be performed by using an operation control apparatus (not shown) to control the operation of the XY motion table 92, moving the apparatus casing 90 in the X directions and the Y directions, scanning the surface of the cornea HC with the radiated spot light, and thereby ablating the corneal surface.

In the light therapy apparatus of the present embodiment, the laser apparatus 1 according to the first embodiment is used, and therefore, even if individual differences arise in the manufacture of the radiation optical system 100, those individual differences can be compensated for by varying the wavelength of the output light of the laser apparatus 1. Furthermore, because the laser apparatus 1 according to the first embodiment is used, the wavelength of the output light of the laser apparatus 1 can be varied over a wide range, which makes it possible to sufficiently compensate for the individual differences even if the individual differences are relatively large.

[Third Embodiment]

Figure 6:
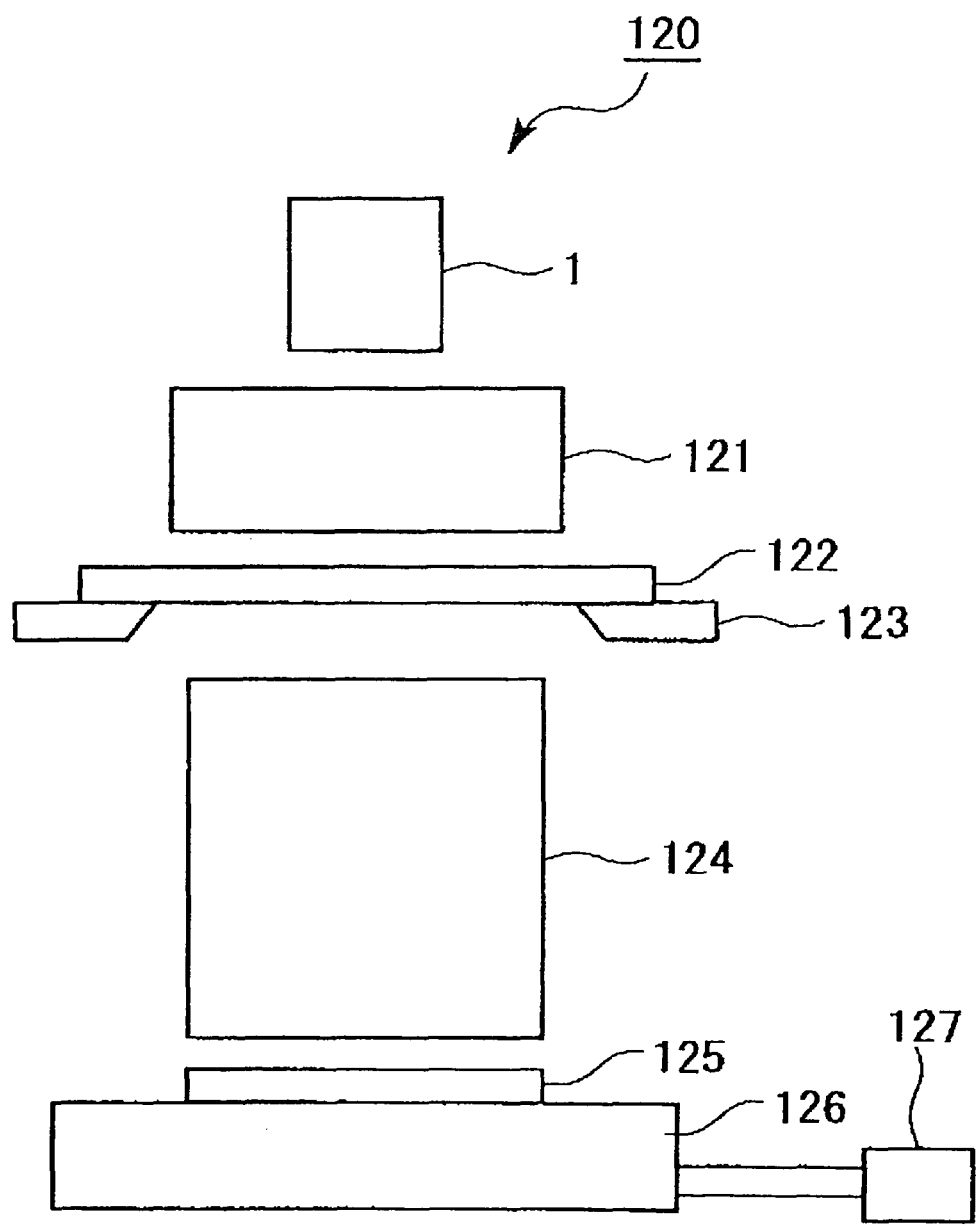
FIG. 6 is a schematic block diagram that schematically shows an exposure apparatus according to a third embodiment of the present invention.

FIG. 6 is a schematic block diagram that schematically shows an exposure apparatus 120 according to a third embodiment of the present invention. The exposure apparatus 120 according to the present embodiment uses the laser apparatus 1 according to the first embodiment and is used by a photolithographic process, which is one of the semiconductor manufacturing processes. An exposure apparatus that is used in a photolithographic process operates on the same principle as that of photoengraving; namely, a device pattern that is precisely drawn on a photomask (i.e., a reticle) is optically projected and transferred to a semiconductor wafer, a glass substrate, and the like, which is coated with a photoresist.

The exposure apparatus 120 according to the present embodiment comprises: the laser apparatus 1 discussed above; a radiation optical system 121 (i.e., an illumination optical system); a mask support platform 123, which supports a photomask 122; a projection optical system 124; a mounting platform 126 whereon a semiconductor wafer 125, which is a photosensitive object and constitutes an exposure target, is mounted and held; and a drive apparatus 127, which moves the mounting platform 126 horizontally.

In the exposure apparatus 120, the output light output from the laser apparatus 1 discussed above enters the radiation optical system 121, which comprises a plurality of lenses, passes therethrough, and then irradiates the entire surface of the photomask 122, which is supported by the mask support platform 123. In the present embodiment, the laser apparatus 1 and the radiation optical system 121 constitute a light radiating apparatus that irradiates the photomask 122, which is the target. The light radiated in this manner and that passes through the photomask 122 contains an image of the device pattern drawn on the photomask 122, and this light transits the projection optical system 124 and is radiated to a prescribed position of the semiconductor wafer 125, which is mounted on the mounting platform 126. At this time, the image of the device pattern of the photomask 122 produced by the projection optical system 124 is reduced and formed on the semiconductor wafer 125, thereby exposing the semiconductor wafer 125.

In the exposure apparatus 120 of the present embodiment, the laser apparatus 1 according to the first embodiment is used, and therefore, even if individual differences arise in the manufacture of the projection optical system 124, those individual differences can be compensated for by varying the wavelength of the output light of the laser apparatus 1. Furthermore, because the laser apparatus 1 according to the first embodiment is used, the wavelength of the output light of the laser apparatus 1 can be varied over a wide range, which makes it possible to sufficiently compensate for the individual differences even if the individual differences are relatively large.

In the device manufacturing method according to one embodiment of the present invention, a semiconductor device is manufactured by: a process that designs the functions and performance of the device; a process that forms a wafer front silicon material; a lithographic process, including a process that uses the exposure apparatus 120 according to the third embodiment to expose the semiconductor wafer 125 via the photomask 122; a process that forms a circuit pattern by, for example, etching; a device assembling process (which includes a dicing process, a bonding process, and a packaging process); and an inspecting process. Furthermore, the present invention is not limited to an exposure apparatus for fabricating semiconductor devices and can also be adapted to exposure apparatuses for fabricating various other devices.

[Fourth Embodiment]

Figure 7:
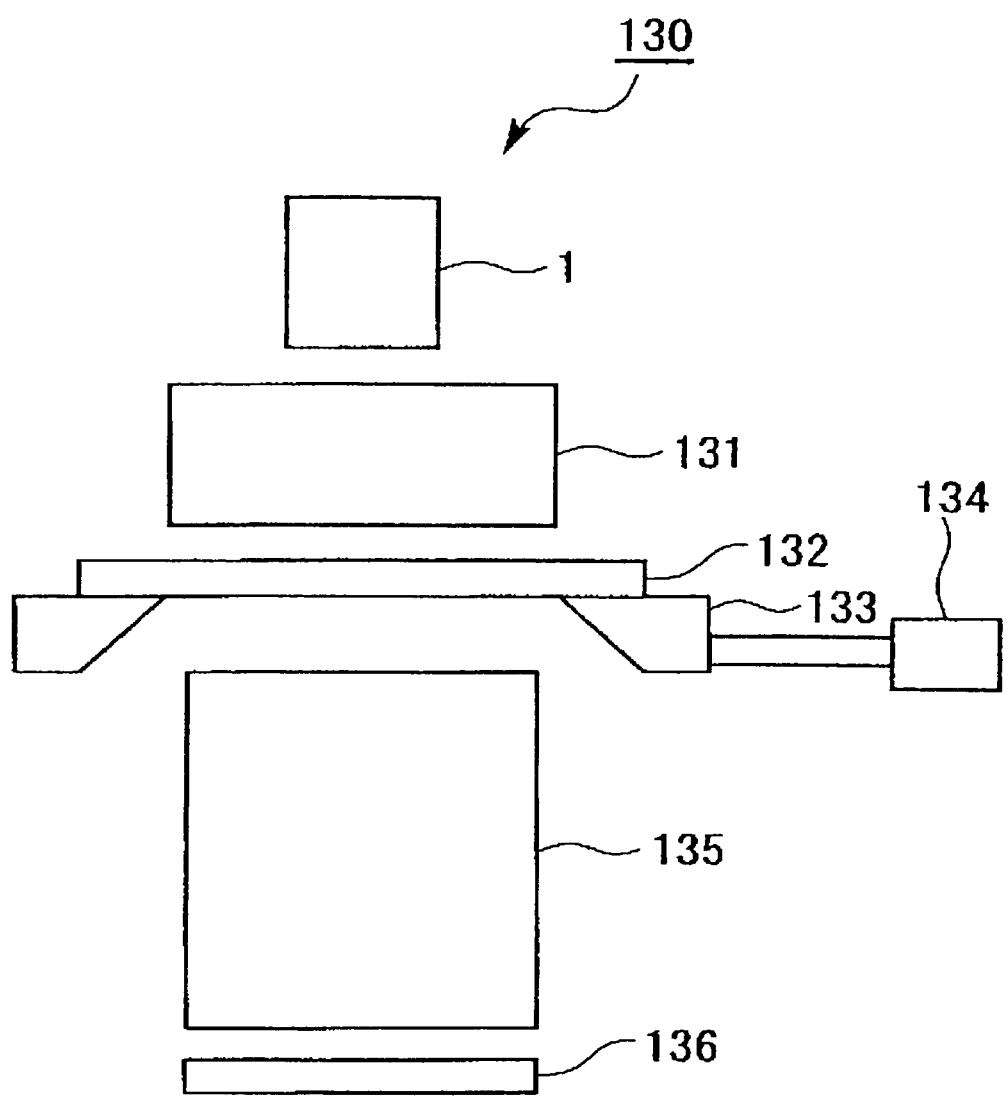
FIG. 7 is a schematic block diagram that shows a mask defect inspection apparatus according to a fourth embodiment of the present invention.

FIG. 7 is a schematic block diagram that shows a mask defect inspection apparatus 130, which serves as an object inspection apparatus, according to a fourth embodiment of the present invention. In the mask defect inspection apparatus 130 according to the present embodiment, a device pattern, which is precisely drawn on a photomask 132, is optically projected onto a TDI (time delay and integration) sensor 136, the sensor image and a prescribed reference image are compared, and any defects in the pattern are identified based on differences between those images.

The mask defect inspection apparatus 130 comprises: the laser apparatus 1 according to the first embodiment; an illumination optical system 131; a mask support platform 133, which supports the photomask 132; a drive apparatus 134, which moves the mask support platform 133 horizontally; a projection optical system 135; and the TDI sensor 136.

In the mask defect inspection apparatus 130, the output light output from the laser apparatus 1 discussed above enters the illumination optical system 131, which comprises a plurality of lenses, passes therethrough, and is radiated to a prescribed area of the photomask 132, which is supported by the mask support platform 133. The light that is radiated in this manner and that passes through the photomask 132 contains an image of the device pattern drawn on the photomask 132; furthermore, this light transits the projection optical system 135 and forms an image at a prescribed position of the TDI sensor 136. Furthermore, the horizontal movement speed of the mask support platform 133 is synchronized to a transfer clock of the TDI sensor 136.

In the mask defect inspection apparatus 130 of the present embodiment, the laser apparatus 1 according to the first embodiment is used, and therefore, even if individual differences arise in the manufacture of the projection optical system 135, those individual differences can be compensated for by varying the wavelength of the output light of the laser apparatus 1. Furthermore, because the laser apparatus 1 according to the first embodiment is used, the wavelength of the output light of the laser apparatus 1 can be varied over a wide range, which makes it possible to sufficiently compensate for the individual differences even if the individual differences are relatively large.

The text above explained the embodiments of the present invention, but the present invention is not limited to these embodiments.

For example, it is obvious that the tuning range of the wavelength of the light output from the laser apparatus 1 is not limited to a range that includes 193.4 nm, which is a wavelength equal to ⅛ of 1.547 μm. In addition, the configuration of the wavelength converting part 30 is not limited to the configuration discussed above.

Furthermore, the second through fourth embodiments were offered merely as examples of apparatuses that use the laser apparatus 1 according to the present invention, and the laser apparatus 1 according to the present invention can be adapted to various other apparatuses. In addition, the second through fourth embodiments discussed above are examples wherein the wavelength tunability of the laser apparatus 1 according to the first embodiment is used to correct the optical system, but the application of the laser apparatus 1 according to the present invention is not limited to such a correction. For example, the laser apparatus 1 according to the present invention may be used in, for example, a measuring apparatus that performs various measurements by radiating light to an object to be measured and analyzing the light reflected therefrom, or to a measuring apparatus that obtains different information about an object to be measured by actively varying the wavelength of the measuring beam; furthermore, the output light of the laser apparatus 1 may be used as the wavelength tunable measuring beam.

EXPLANATION OF SYMBOLS

1 Laser apparatus
2 Fundamental wavelength light generating unit
11a, 31a, 32a, 34a, 37a, 39a, 40a Temperature regulators
11b, 31b, 32b, 34b, 37b, 39b, 40b Temperature detectors
20 Optical amplifier unit
30 Wavelength converting part
31, 32, 34, 37, 39, 40 Nonlinear optical crystals
50 Main control unit
60 Correspondence information storage unit
70 Temperature control unit
80 Light therapy apparatus
120 Exposure apparatus
130 Mask defect inspection apparatus

The invention claimed is:

1. A laser apparatus that outputs wavelength tunable output light, comprising:
    a fundamental wavelength light generating unit, which generates light of the fundamental wavelength in accordance with an output wavelength instruction signal that specifies the wavelength of the output light;
    an optical amplifier unit, which amplifies the light of the fundamental wavelength;
    a wavelength converting part that comprises a plurality of nonlinear optical crystals, each nonlinear optical crystal performing wavelength conversion, each non-linear optical crystal having a corresponding temperature regulator, each temperature regulator regulating the temperature of the corresponding nonlinear optical crystal, wherein the wavelength converting part converts the light amplified by the optical amplifier unit to light of the wavelength indicated by the output wavelength instruction signal;
    a storage unit, which stores correspondence information that indicates a correspondence relationship between the wavelength of the output light and the temperature of each of the non-linear optical crystals to be set in accordance with the corresponding wavelength; and
    a control unit that controls each of the temperature regulators such that the temperature of the corresponding nonlinear optical crystal reaches the temperature to be set as determined by the correspondence information in accordance with the output wavelength instruction signal.

2. A laser apparatus according to claim 1, wherein the fundamental wavelength light generating unit comprises a wavelength tunable laser light source.

3. A laser apparatus according to claim 2, wherein the wavelength tunable laser light source comprises a laser light source temperature regulator and generates light of an oscillation wavelength corresponding to the temperature regulated by the laser light source temperature regulator as the light of the fundamental wavelength;
    the storage unit stores correspondence information that indicates the correspondence relationship between the wavelength of the output light and the temperature of the wavelength tunable laser light source to be set in accordance with that wavelength; and
    the control unit controls the laser light source temperature regulator such that the temperature of the wavelength tunable laser light source reaches the temperature to be set as determined by the correspondence information in accordance with the output wavelength instruction signal.

4. A light therapy apparatus, comprising:
    a laser apparatus according to claim 3; and
    a radiation optical system, which guides and radiates light output from the laser apparatus to a therapy region.

5. An exposure apparatus, which transfers a pattern of a mask to a photosensitive object, comprising:
    a laser apparatus according to claim 3;
    an illumination optical system, which radiates light output from the laser apparatus to the mask; and
    a projection optical system, which projects light from the mask to the photosensitive object.

6. An object inspection apparatus, comprising:
    a laser apparatus according to claim 3;
    a support part, which supports an object to be inspected;
    a detector, which detects a projected image of the object to be inspected;
    an illumination optical system, which radiates light output from the laser apparatus to the object to be inspected; and
    a projection optical system, which projects light from the object to be inspected to the detector.

7. A light therapy apparatus, comprising:
    a laser apparatus according to claim 2; and
    a radiation optical system, which guides and radiates light output from the laser apparatus to a therapy region.

8. An exposure apparatus, which transfers a pattern of a mask to a photosensitive object, comprising:
    a laser apparatus according to claim 2;
    an illumination optical system, which radiates light output from the laser apparatus to the mask; and
    a projection optical system, which projects light from the mask to the photosensitive object.

9. An object inspection apparatus, comprising:
    a laser apparatus according to claim 2;
    a support part, which supports an object to be inspected;
    a detector, which detects a projected image of the object to be inspected;
    an illumination optical system, which radiates light output from the laser apparatus to the object to be inspected; and
    a projection optical system, which projects light from the object to be inspected to the detector.

10. A light therapy apparatus, comprising:
    a laser apparatus according to claim 1; and
    a radiation optical system, which guides and radiates light output from the laser apparatus to a therapy region.

11. An exposure apparatus, which transfers a pattern of a mask to a photosensitive object, comprising:
    a laser apparatus according to claim 1;
    an illumination optical system, which radiates light output from the laser apparatus to the mask; and
    a projection optical system, which projects light from the mask to the photosensitive object.

12. A device fabricating method, which includes a lithographic process, comprising the step of:
    using the exposure apparatus according to claim 11 to transfer, in the lithographic process, the pattern of the mask to the photosensitive object.

13. An object inspection apparatus, comprising:
    a laser apparatus according to claim 1;
    a support part, which supports an object to be inspected;
    a detector, which detects a projected image of the object to be inspected;

an illumination optical system, which radiates light output from the laser apparatus to the object to be inspected; and a projection optical system, which projects light from the object to be inspected to the detector.

* * * * *